(12) United States Patent
Mir et al.

(10) Patent No.: US 9,095,380 B2
(45) Date of Patent: Aug. 4, 2015

(54) SPINOUS PROCESS CROSS-LINK

(76) Inventors: Hamid R. Mir, Santa Monica, CA (US); John E. Hammill, Sr., Maumee, OH (US); Robert L. Doubler, Monroe, MI (US)

( * ) Notice: Subject to any disclaimer, the term of this patent is extended or adjusted under 35 U.S.C. 154(b) by 0 days.

(21) Appl. No.: 13/214,806

(22) Filed: Aug. 22, 2011

(65) Prior Publication Data

US 2011/0307012 A1    Dec. 15, 2011

Related U.S. Application Data

(63) Continuation-in-part of application No. 12/415,010, filed on Mar. 31, 2009.

(51) Int. Cl.
*A61B 17/70* (2006.01)
*A61F 2/44* (2006.01)

(52) U.S. Cl.
CPC ......... *A61B 17/7052* (2013.01); *A61B 17/7062* (2013.01)

(58) Field of Classification Search
CPC ........... A61B 17/7049; A61B 17/7062; A61B 17/7052; A61B 17/7043
USPC ........................ 606/246, 248–253; 623/17.11
See application file for complete search history.

(56) References Cited

U.S. PATENT DOCUMENTS

| | | | |
|---|---|---|---|
| 3,648,691 A | 3/1972 | Lumb et al. | |
| 4,722,870 A | 2/1988 | White | |
| 5,702,452 A * | 12/1997 | Argenson et al. | 606/253 |
| 6,217,578 B1 | 4/2001 | Crozet et al. | |
| 6,364,883 B1 | 4/2002 | Santilli | |
| 6,402,751 B1 * | 6/2002 | Hoeck et al. | 606/252 |
| 6,419,703 B1 | 7/2002 | Fallin et al. | |
| 6,454,767 B2 | 9/2002 | Alleyne | |
| 6,579,319 B2 | 6/2003 | Goble et al. | |
| 6,592,585 B2 | 7/2003 | Lee et al. | |
| 6,669,729 B2 | 12/2003 | Chin | |
| 6,866,664 B2 * | 3/2005 | Sch.ang.r et al. | 606/252 |
| 6,902,580 B2 | 6/2005 | Fallin et al. | |
| 7,041,136 B2 | 5/2006 | Goble et al. | |
| 7,048,736 B2 | 5/2006 | Robinson et al. | |
| 7,066,938 B2 | 6/2006 | Slivka et al. | |
| 7,090,698 B2 | 8/2006 | Goble et al. | |
| 7,264,620 B2 | 9/2007 | Taylor | |
| 7,282,064 B2 | 10/2007 | Chin | |
| 7,335,203 B2 | 2/2008 | Winslow et al. | |
| 7,377,942 B2 | 5/2008 | Berry | |
| 7,476,251 B2 | 1/2009 | Zucherman et al. | |
| 7,566,345 B1 | 7/2009 | Fallin et al. | |
| 7,645,294 B2 | 1/2010 | Kalfas et al. | |
| 7,708,778 B2 | 5/2010 | Gordon et al. | |
| 7,727,233 B2 | 6/2010 | Blackwell et al. | |

(Continued)

*Primary Examiner* — Eduardo C Robert
*Assistant Examiner* — Jacqueline Johanas
(74) *Attorney, Agent, or Firm* — McHale & Slavin, P.A.

(57) ABSTRACT

A prosthetic spinous process cross-link implant for the replacement of a posterior vertebral element. The implant includes a cross link body member with a pair of adjustable link arms connected to the cross link body to size the implant to specific anatomical configurations. The implant includes a rod clamp that is spring loaded to a forward position such that capturing a spinal rod on to the adjustable link arms to achieve a snap on effect thereby increasing the ease of installation. A plurality of spinous process cross-link implants can be assembled as a kit wherein the set includes a group of spinous process type yokes and bridge type yokes each group including both fixed and variable sized implants.

15 Claims, 13 Drawing Sheets

(56) References Cited

U.S. PATENT DOCUMENTS

| | | | |
|---|---|---|---|
| 7,744,632 B2* | 6/2010 | Usher | 606/250 |
| 7,780,704 B2* | 8/2010 | Markworth et al. | 606/253 |
| 7,794,478 B2* | 9/2010 | Nilsson | 606/251 |
| 7,806,911 B2 | 10/2010 | Peckham | |
| 7,862,591 B2 | 1/2011 | Dewey et al. | |
| 7,922,747 B2* | 4/2011 | Kirschman | 606/251 |
| 7,927,355 B2* | 4/2011 | Berrevoets et al. | 606/250 |
| 7,959,653 B2* | 6/2011 | Thramann et al. | 606/250 |
| 8,192,467 B2* | 6/2012 | Felix et al. | 606/250 |
| 8,226,688 B2* | 7/2012 | Alain | 606/248 |
| 8,292,924 B2* | 10/2012 | Neary et al. | 606/250 |
| 8,597,331 B2* | 12/2013 | McAfee | 606/248 |
| 8,840,646 B2* | 9/2014 | Vittur et al. | 606/247 |
| 2004/0176765 A1* | 9/2004 | Troxell et al. | 606/61 |
| 2005/0070932 A1 | 3/2005 | Falahee | |
| 2005/0080486 A1 | 4/2005 | Fallin et al. | |
| 2005/0090821 A1* | 4/2005 | Berrevoets et al. | 606/61 |
| 2005/0149021 A1 | 7/2005 | Tozzi | |
| 2005/0177162 A1 | 8/2005 | McLeod et al. | |
| 2005/0228377 A1* | 10/2005 | Chao et al. | 606/61 |
| 2005/0245929 A1 | 11/2005 | Winslow et al. | |
| 2006/0004449 A1 | 1/2006 | Goble et al. | |
| 2006/0004451 A1 | 1/2006 | Goble et al. | |
| 2006/0015181 A1* | 1/2006 | Elberg | 623/16.11 |
| 2006/0036246 A1 | 2/2006 | Carl et al. | |
| 2006/0058790 A1 | 3/2006 | Carl et al. | |
| 2006/0161154 A1* | 7/2006 | McAfee | 606/61 |
| 2006/0217718 A1 | 9/2006 | Chervitz et al. | |
| 2006/0241601 A1* | 10/2006 | Trautwein et al. | 606/61 |
| 2006/0265069 A1 | 11/2006 | Goble et al. | |
| 2006/0271045 A1* | 11/2006 | Hubbard et al. | 606/61 |
| 2006/0271051 A1* | 11/2006 | Berrevoets et al. | 606/61 |
| 2007/0233068 A1* | 10/2007 | Bruneau et al. | 606/61 |
| 2007/0270812 A1 | 11/2007 | Peckham | |
| 2008/0021471 A1 | 1/2008 | Winslow et al. | |
| 2008/0021472 A1 | 1/2008 | Winslow et al. | |
| 2008/0027436 A1* | 1/2008 | Cournoyer et al. | 606/61 |
| 2008/0172093 A1* | 7/2008 | Nilsson | 606/250 |
| 2008/0177315 A1* | 7/2008 | Usher | 606/253 |
| 2008/0177327 A1* | 7/2008 | Malandain et al. | 606/278 |
| 2008/0183211 A1 | 7/2008 | Lamborne et al. | |
| 2008/0281360 A1 | 11/2008 | Vittur et al. | |
| 2008/0281361 A1 | 11/2008 | Vittur et al. | |
| 2010/0010545 A1* | 1/2010 | Park et al. | 606/278 |
| 2010/0174315 A1 | 7/2010 | Scodary et al. | |
| 2010/0217322 A1 | 8/2010 | Predick | |
| 2010/0249842 A1* | 9/2010 | Mir | 606/250 |
| 2010/0274286 A1* | 10/2010 | Blain et al. | 606/250 |
| 2010/0305612 A1* | 12/2010 | Nilsson | 606/250 |
| 2011/0022090 A1 | 1/2011 | Gordon et al. | |
| 2011/0098751 A1 | 4/2011 | Ani et al. | |
| 2012/0095511 A1* | 4/2012 | Nihalani | 606/250 |
| 2012/0158060 A1 | 6/2012 | Abrahams et al. | 606/248 |
| 2012/0253397 A1* | 10/2012 | Kraus | 606/250 |

* cited by examiner

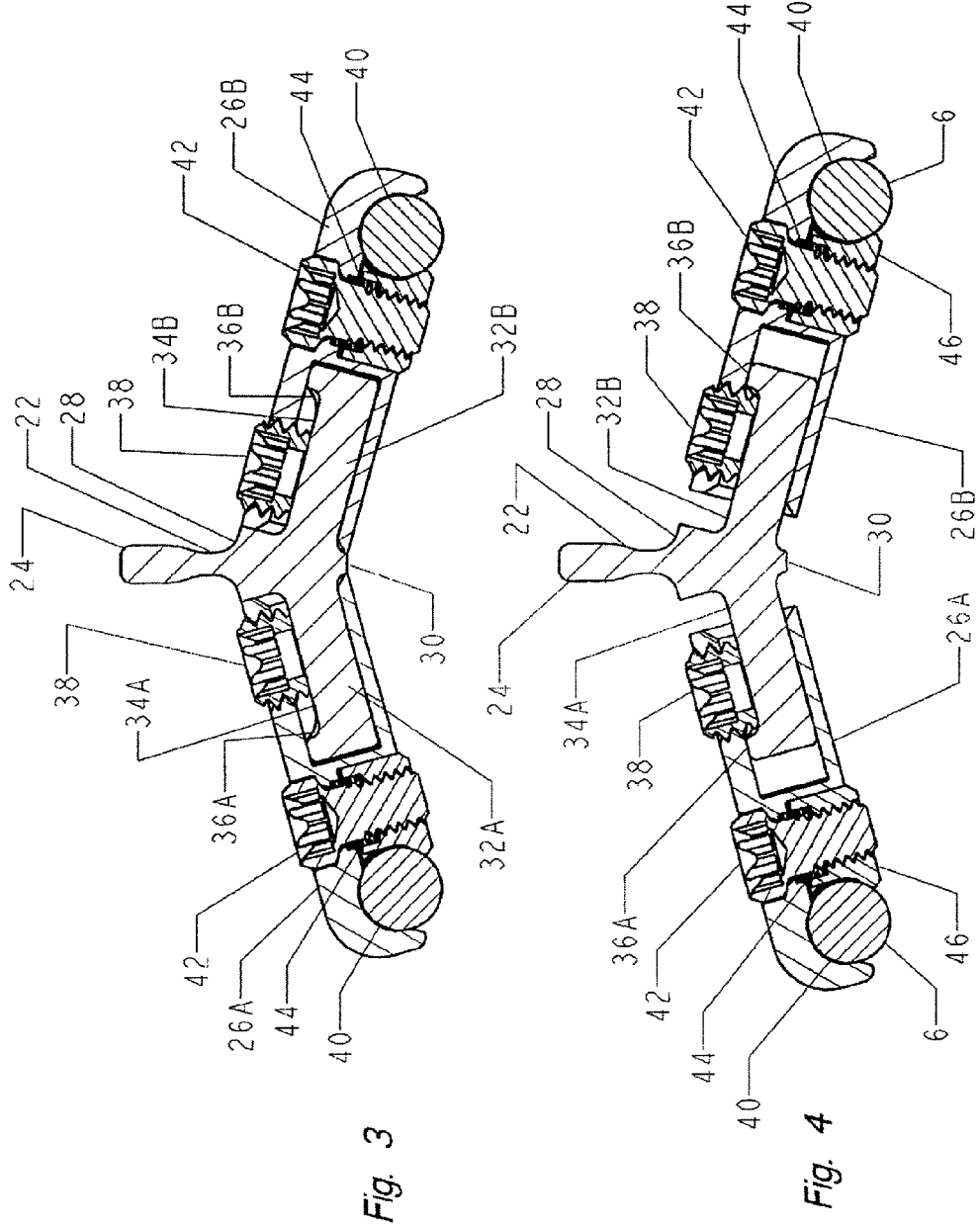

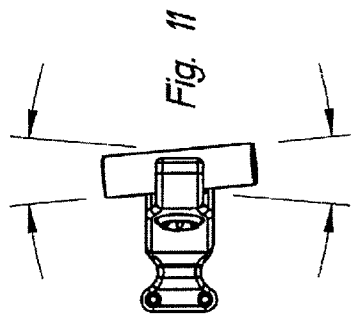
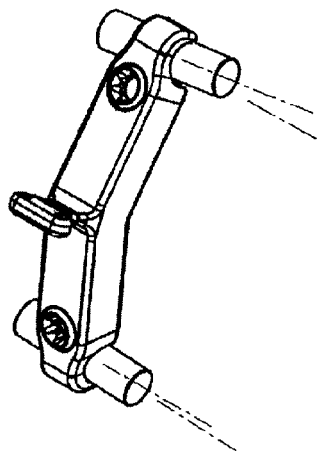
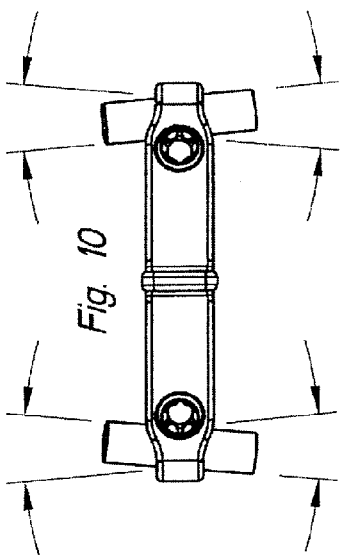
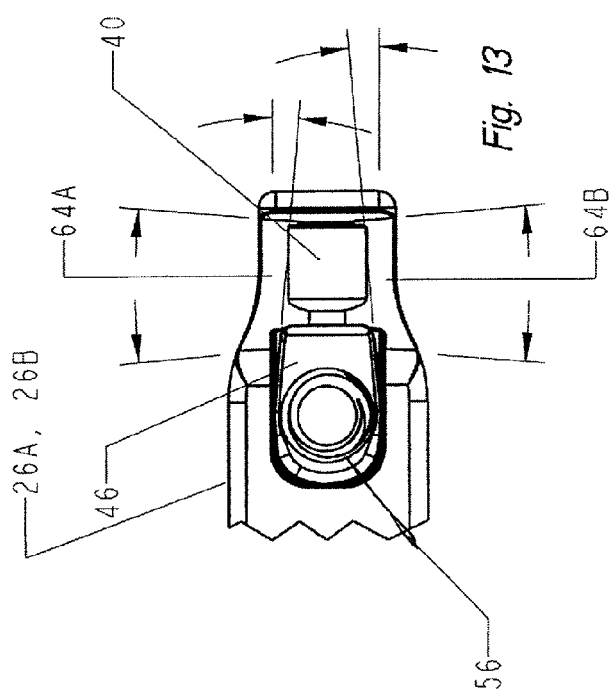

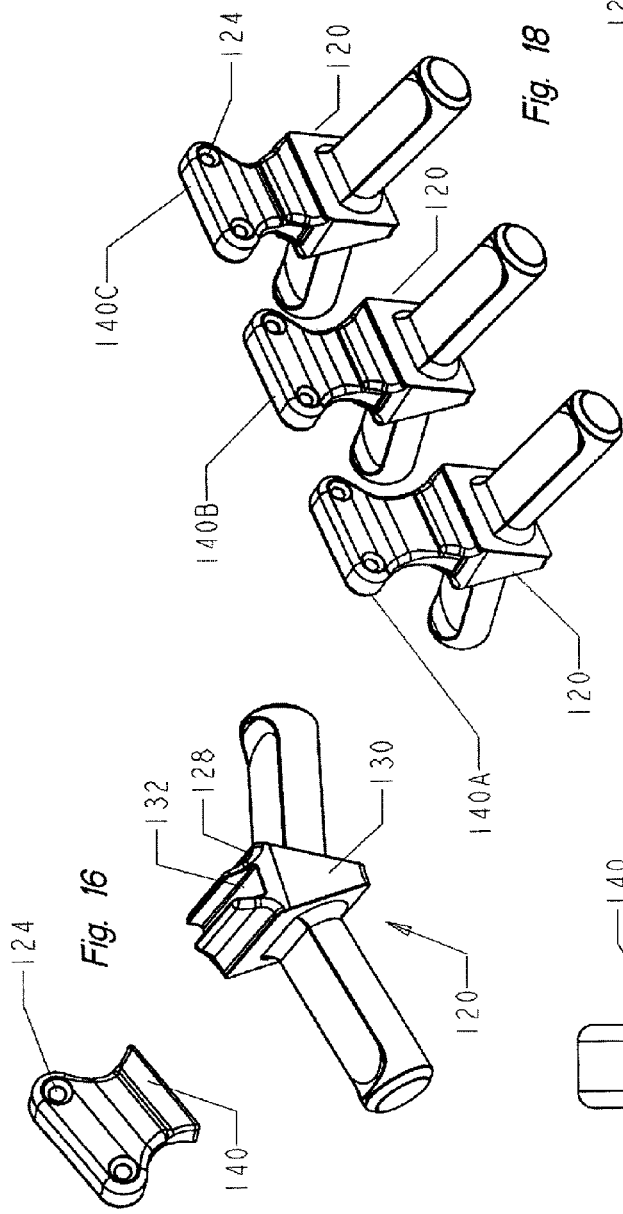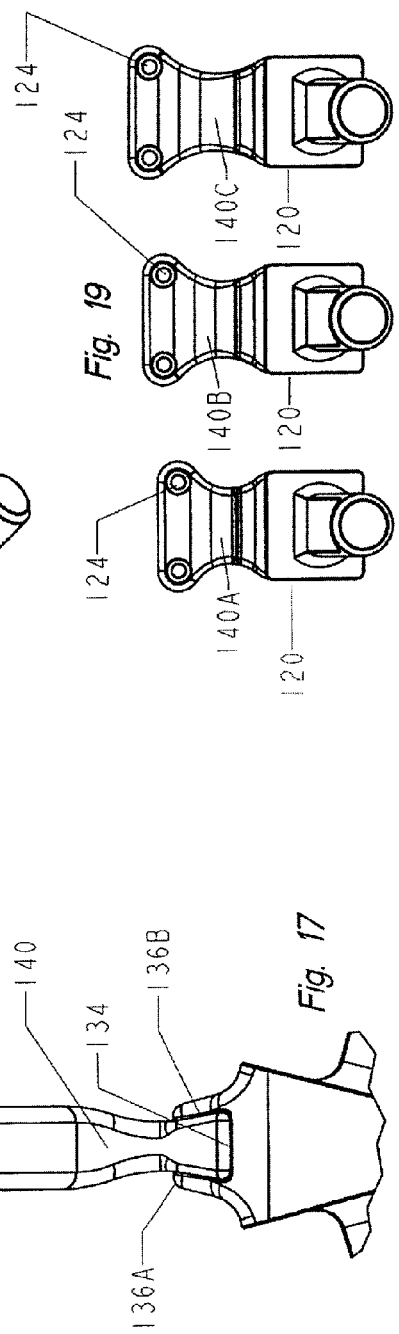

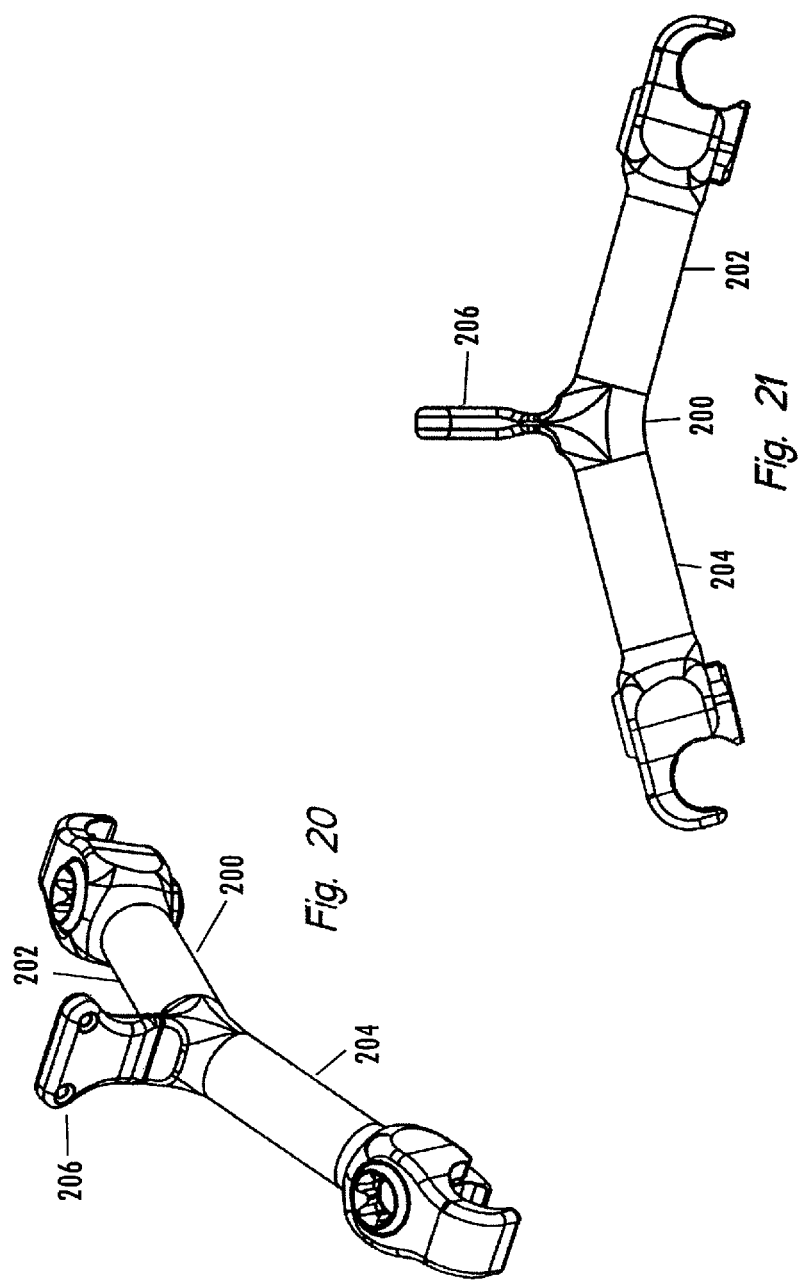

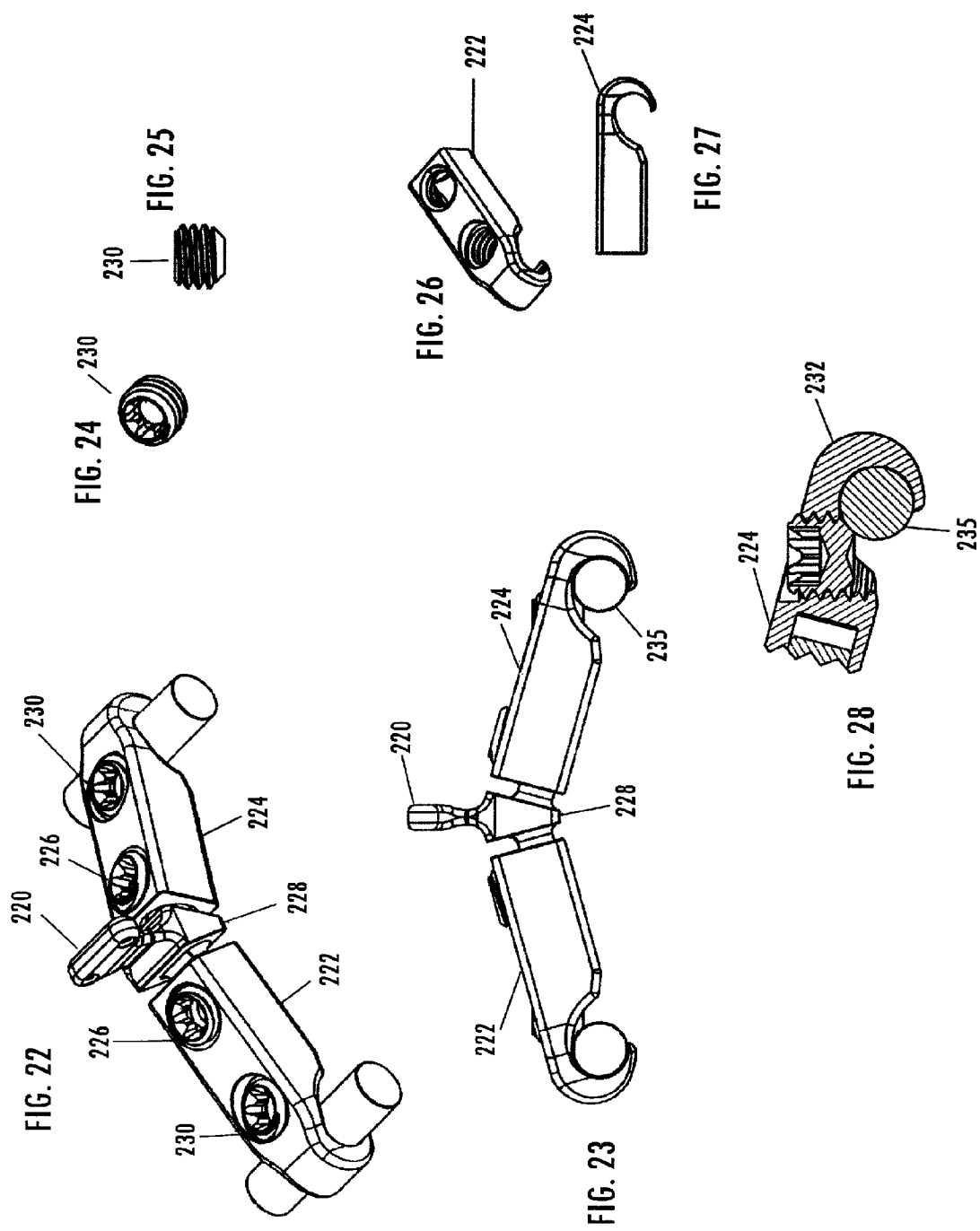

SPINOUS PROCESS CROSS-LINK

CROSS REFERENCE TO RELATED APPLICATION

This application is a continuation-in-part of U.S. patent application Ser. No. 12/415,010, filed on Mar. 31, 2009, the entire contents of which is hereby expressly incorporated by reference.

FIELD OF THE INVENTION

The present invention relates generally to surgical implants, and more particularly to implants that replace posterior vertebral elements such as a natural lamina and a natural spinous process.

BACKGROUND OF THE INVENTION

Implantable surgical devices are known and used in many different applications, including spinal surgery. A prosthetic device may be attached to a posterior section of a vertebra to mimic a natural vertebral element. In one example, an implantable prosthetic device is attached to the posterior vertebra by screws and designed to replace the natural lamina, the natural spinous process, all four natural facets, and may also replace the natural transverse processes. However, during a lumbar laminectomy, only the lamina and spinous process are removed, as opposed to the complete spinal vertebra. Thus, there is a continuing need for a prosthetic device that replaces only the lamina and spinous process.

Examples of a device of this general type are disclosed in U.S. Pat. Nos. 6,419,703, 6,902,580 and 7,566,345 to Fallin, that disclose a prosthetic replacement for a posterior element of a vertebra comprising portions that replace the natural lamina and the four natural facets. The prosthetic replacement may also include portions that replace one or more of the natural spinous process and the two natural transverse processes. If desired, the prosthesis replacement may also replace the natural pedicles.

U.S. Published Application 2008/0,281,361 to Vittur et al, discloses a posterior stabilization device that includes first and second elongate elements engageable along the spinal column and a spinous process replacement body positionable between the elongate elements. Connection mechanisms are provided to adjustably connect the spinous process replacement device to the elongate elements so that the spinous process replacement device can be moved to the desired location between the connecting elements and secured in the desired location.

U.S. Pat. No. 7,377,942 discloses a prosthetic device for interposition in a space left by one or more excised vertebral posterior structures. The prosthetic device comprises a lamina bridge having an inferior portion for replacing an excised lamina; at least one inferior facet replacement device, connected to the inferior portion of the lamina bridge, to replace an excised inferior articular process; and at least one superior facet replacement device to replace an excised superior articular process. The at least one superior facet replacement device articulates with the at least one inferior facet replacement device.

Additionally, U.S. Pat. No. 7,090,698 discloses a prosthesis for the replacement of the cartilaginous structures of a spine motion segment is described. The prosthesis comprises an intervertebral disc prosthesis in combination with a facet joint prosthesis.

U.S. Publication Number 2010/0174315 discloses a device for covering and protecting the spinal cord of a patient after some or all of the spinous process or lamina has been removed. The device includes a main body adjustably attached to at least two rod attachment flanges such that each rod attachment flange may be adjusted closer and further from the main body. The rod attachment flanges are each attached to a pedicle rod having at least four pedicle screws attached thereto. The pedicle attachment screws are adapted for attachment to at least one vertebrae of the patient.

U.S. Publication Number 2005/0149021 discloses a spinal implant device having an anatomical shape designed to mimic and restore normal human spinal anatomy. The devices come in a range of sizes and are structured to specifically accommodate the structure of at least one of the cervical, thoracic and lumbar regions of the spine. Once affixed to the vertebrae, the devices may be used to effectively fuse two or more vertebrae, or to stabilize the vertebrae and protect the posterior portions of the spinal cord. Adjustments for sagittal plane contouring may also be effected through cable tensioning via spinous process fixation.

U.S. Pat. No. 7,066,938 discloses an implantable medical connector device that employs a snap-on technology to safely and easily mate with another device. The medical connector device generally includes an elongate member having first and second connector members formed on opposed ends thereof Each connector member includes an opening formed in a sidewall thereof and extending into a nesting seat. The nesting seat is adapted to seat and engage an implanted cylindrical element.

U.S. Pat. No. 6,592,585 discloses an apparatus for fixing the spine, and particularly to a spine fixing apparatus for fixing an unstable spine, caused by a fracture or a disease, to be properly collaborated together such that the spine can recover its stable state. The device provides a spine fixing apparatus, comprising a plurality of spine screw members combined to the spine with a certain distance; a pair of rods detachably combined to the spine screw members, the rods connecting and supporting the spine screw members; pressing members detachably combined to the spine screw members, the pressing member pressing the rod toward the spine screw member; and a connecting device integrally combined to the pressing member, the connecting device flexibly connecting the spine screw members.

U.S. Pat. No. 6,454,767 discloses a spinal protection device which minimizes the formation of post-operative adhesions. The protection device may comprise a fenestrated shield, and may be positioned such that contact between the shield and the spinal dura is substantially avoided.

U.S. Pat. No. 7,264,620 discloses a vertebral implant comprising a first base configured for securing to a first cut portion of a vertebra, and second base configured for securing to a second cut portion of the vertebra. A connecting member is configured to associate the first and second bases at a preselected spacing from each other, and the implant is preferable adjustable to select the spacing.

While various attempts have been made to provide a spinal implants none have disclosed a prosthetic spinous process cross-link that have recognized and solved the problems associated with these devices as disclosed by the inventors of the instant invention.

BRIEF SUMMARY OF THE INVENTION

The following presents a simplified summary of the invention in order to provide a basic understanding of some example aspects of the invention. This summary is not an extensive overview of the invention. Moreover, this summary is not intended to identify critical elements of the invention nor delineate the scope of the invention. The sole purpose of the summary is to present some concepts of the invention in simplified form as a prelude to the more detailed description that is presented later.

In accordance with one aspect of the present invention, a prosthetic spinous process cross-link, hereinafter referred to as "implant", for the replacement of a posterior vertebral element is provided. Posterior vertebral element is defined as posterior spinous process and the lamina. The vertebral element includes a natural lamina extending from a pair of natural pedicles and a natural spinous process extending from the lamina. The implant includes a first pair and a second pair of screws attached to a vertebral body and a first rod and a second rod, the first rod extending between the first pair of screws and the second rod extending between the second pair of screws. A prosthetic lamina attached to the rods is also provided, along with a prosthetic spinous process extending from the prosthetic lamina.

In accordance with another aspect of the present invention the implant includes a first pair of C-shaped gripping portions that attach the implant to the vertebral body using a first rod and a second rod, the first rod extending between a first pair of screws and the second rod extending between a second pair of screws. A prosthetic lamina attached to the rods is also provided, along with a prosthetic spinous process extending from the prosthetic lamina.

In accordance with another aspect of the present invention the implant includes a mounting assembly attached to a vertebral body. The implant consists of a prosthetic lamina and prosthetic spinous process along with at least one aperture extending through the prosthetic spinous process.

In accordance with yet another aspect of the present invention the implant includes a cross link body member with a pair of adjustable link arms connected to the cross link body to size the implant to specific anatomical configurations.

In accordance with still another aspect of the present invention the implant includes a rod clamp that is spring loaded to a forward position such that capturing the spinal rod on to the adjustable link arms can be achieved with a snap on effect thereby increasing the ease of installation.

In accordance with another aspect of the present invention the adjustable arms of the implant each have a C-shaped clamp including conical surfaces to permit a conical zone of adjustment between the spinal rod and the C shaped clamp.

In accordance with another aspect of the present invention the rod clamp is pivotally positioned within the adjustable link arm to provide a degree of adjustability between the spinal rod and the implant.

In accordance with another aspect of the present invention the implant can be constructed as a kit wherein the kit includes implants of varying sizes and can be of the fixed type or the adjustable type, and either or both may include a spinous process type yoke or a bridge type yoke.

In accordance with still another aspect of the present invention the implant includes a modular yoke arrangement that permits the yoke to be used with various sized and shaped spinal process inserts.

BRIEF DESCRIPTION OF THE DRAWINGS

The foregoing and other aspects of the present invention will become apparent to those skilled in the art to which the present invention relates upon reading the following description with reference to the accompanying drawings, in which:

FIG. 3 is a cross sectional side view of the spinous process cross-link implant with the adjustable link arms in their fully retracted position.

FIG. 4 is a cross sectional side view of the spinous process cross-link implant with the adjustable link arms in their fully extended position.

FIG. 10 is a top view of the spinous process implant and illustrating the adjustable orientation of the spinal rods to the adjustable link arms due to the conical surfaces within each of the C shaped clamps.

FIG. 11 is a side view of the spinous process implant and illustrating the adjustable orientation of the spinal rods to the adjustable link arms due to the conical surfaces within the C-shaped clamps.

FIG. 12 is a perspective view of the spinous process implant and illustrating the adjustable orientation of the spinal rods to the adjustable link arms due to the conical surfaces within the C-shaped clamps.

FIG. 13 is bottom view of an adjustable link arm showing the conical surfaces within the C-shaped opening and the rod clamp that is positioned within a recess formed in the lower surface of the link arm.

FIG. 16 is an exploded perspective view of a spinal process insert and a yoke body with an insert pocket.

FIG. 17 is a front view of showing the spinal process insert within a pocket formed on the yoke body.

FIG. 18 is a perspective view of several yoke bodies each having a spinal process insert of varying profile and vertical height.

FIG. 19 is a side view of the yoke bodies of FIG. 18 each having a spinal process insert of varying profile and height.

FIG. 20 is a perspective view of the yoke with fixed link arms.

FIG. 21 is a side view FIG. 20.

FIG. 22 is a perspective view of the yoke with adjustable link arm with conventional set screw attachments.

FIG. 23 is a side view of FIG. 22.

FIG. 24 is a perspective view of the set screw.

FIG. 25 is a side view of FIG. 24.

FIG. 26 is a perspective view of the link arm.

FIG. 27 is side view of FIG. 26.

FIG. 28 is a cross sectional side view of the link arm set screw secured to a rod.

FIG. 30 is a side view of the yoke bodies of FIG. 18 each having a spinal process insert of varying profile and height.

FIG. 31 is a side view of the yoke bodies of FIG. 18 each having a spinal process insert of varying profile and height.

DETAILED DESCRIPTION OF THE INVENTION

Figure 1:
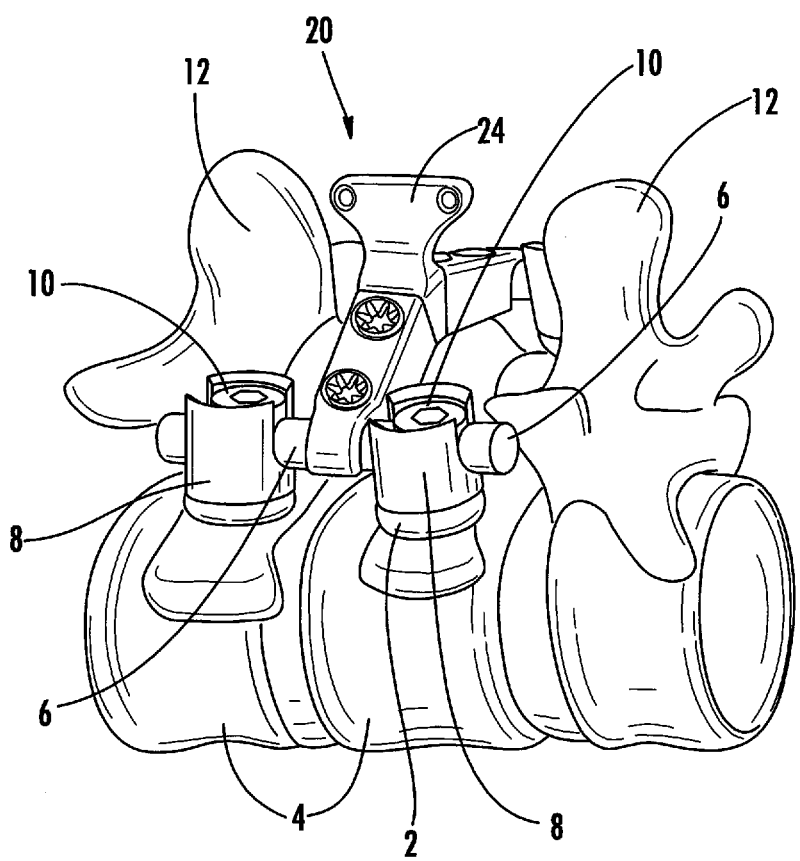
FIG. 1 illustrates a side view of the spinous process cross-link implant that replaces the lamina and spinous process.

Example embodiments that incorporate one or more aspects of the present invention are described and illustrated in the drawings. These illustrated examples are not intended to be a limitation on the present invention. For example, one or more aspects of the present invention can be utilized in other embodiments and even other types of devices. Moreover, certain terminology is used herein for convenience only and is not to be taken as a limitation on the present invention. Still further, in the drawings, the same reference numerals are employed for designating the same elements.

Turning to the shown example of FIG. 1, at lest two pair of pedicle screws 2 and nut assemblies 8 are driven through sides of adjacent vertebral bodies 4. Once the pedicle screws 2 are secured, a spinal rod 6 may be inserted through an opening in the nut assembly 8. The spinal rods 6 are then held in place by a locking mechanism 10 which locks into the nut assembly 8. Each of the spinal rods 6 extends between the pair of adjacent pedicle screws 2 with the rods 6 on opposite sides of the spinous process 12 and are substantially parallel to each other. A spinous process cross-link implant 20 includes a pair of link arms wherein each arms is attached to one of the spinal rods 6. In the final position, the spinous process cross-link implant 20 is placed in the void where the lumbar laminectomy procedure has occurred and is situated between two natural spinous processes 12.

The spinous process cross-link implant 20 may further act as a location for the placement of bone. Bone may be laid on top of the prosthesis, including on the cross-link body, each of the link arms and other components. The prosthesis can be made from materials that can enhance or promote bony on growth. This may include materials including, but not limited to, hydroxyapatite, titanium mesh, etc. The bone placed on the prosthesis and the associated parts allows for regrowth of the bone and fortification of the fusion mass across the levels.

The mounting assembly and method described above is merely one of a number of potential mounting assemblies and methods. Various mounting assemblies, including, but not limited to the pedicle screw 2 and spinal rod 6 assembly, are also contemplated. For instance, in one embodiment, the pedicle screws 2 alone may constitute the mounting assembly, as the spinous process cross-link implant 20 may be attached directly to the pedicle screws 2. In such an embodiment, the rods 6 may not be used and the link arms may be secured directly to the pedicle screws 2 as opposed to the rods 6. In yet another embodiment, each link arm may constitute a mounting assembly, as each link arm may have a screw portion instead of the C-shaped gripping portion. In such an embodiment, the screw portions may screw directly into the vertebral body 4, thus eliminating the need for both the pedicle screws 2 and rods 6. As shown in FIG. 1, the pedicle screws 2 may be inserted into more than one vertebral body 4 with the rods 6 extending there between. In a similar but different embodiment, a plurality of pedicle screws 2 may be inserted into a single vertebral body 4. Thus, rods 6 may still be used to extend between the pedicle screws 2 and allow for the C-shaped gripping portion to be attached to the rods 6. In this instance, both the pedicle screws 2 and rods 6 may constitute the mounting assembly as the laminectomy may be performed without a spinal fusion. The spinous process cross-link implant 20 will then act to protect and identify the dura, but will not cause vertebral bodies to be fused together.

Figure 2:
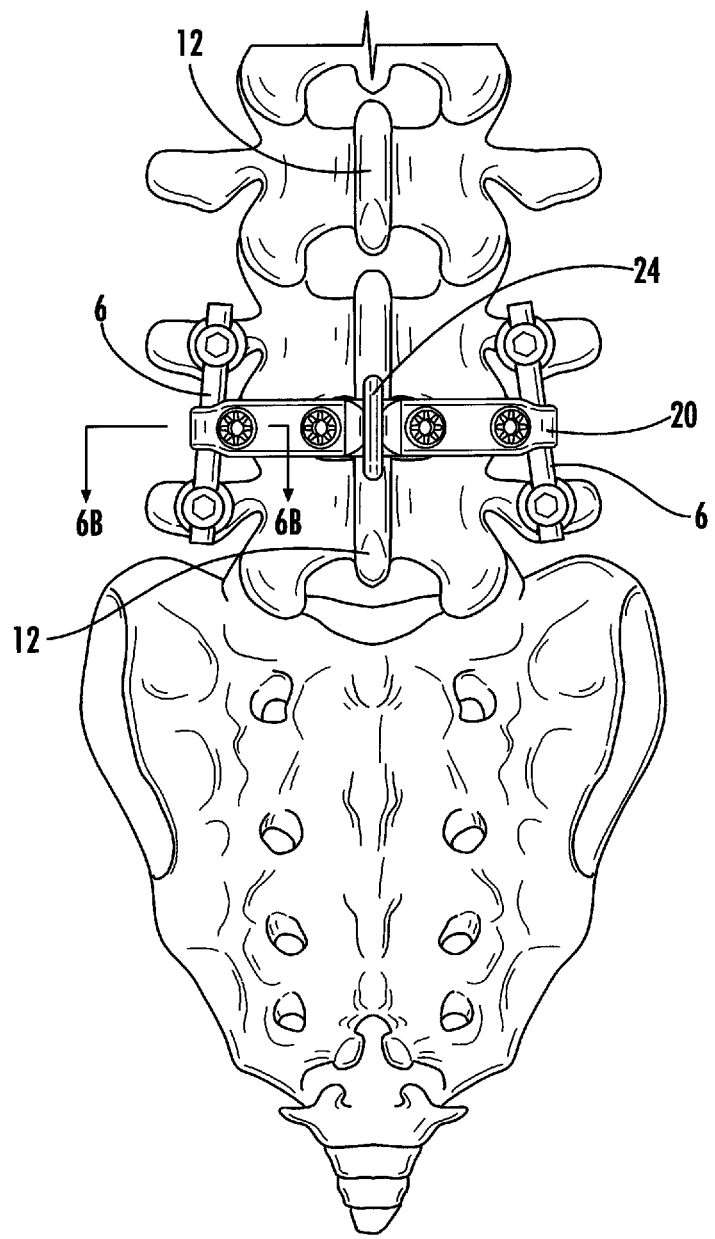
FIG. 2 illustrates a posterior view of the spinous process cross-link implant of FIG. 1.

Referring now to FIG. 2, there is shown a side view of the spinous process cross-link implant 20 attached to the vertebral body 4 after the lumbar laminectomy procedure. The spinous process cross-link implant 20 includes a prosthetic spinous process 22 that may include one or more apertures 24 extending through. After the spinous process cross-link implant 20 is implanted on the vertebral body 4, the lumbar fascia and paraspinal muscles remain detached. The apertures 24 allow sutures to pass through for closure and reattachment of the lumbar fascia and paraspinal muscles following the lumbar laminectomy procedure. Once the lumbar fascia are closed, the paraspinal muscles may be brought back to their normal position adjacent to the spinous process cross-link implant 20 and the prosthetic spinous process 22.

FIG. 3 is a cross sectional side view of the spinous process cross-link implant 20 with a pair of adjustable link arms 26A and 26B in their fully retracted position. Cross-link implant 20 includes a cross link body 28. Cross-link body 28 includes a central portion 30 that is generally wedge shaped in cross section as well as a first leg 32A that is diametrically opposed to a second leg 32B. Located above the central portion 28 is the prosthetic spinous process 22 that includes a plurality of apertures 24. The upper surface of first and second leg 32A and 32B is formed with a notch 34A and 34B, respectively. At the distal end of each leg portion 32A and 32B is an upstanding end portion 36A and 36B which serves a stop element as will be described below. A set screw 38 is threaded through an upper surface of link arms 26A and 26B. The distal end of set screws 38 is configured to engage the surface within notches 34A and 34B when the set screws are tightened down. The proximal ends of set screws 38 are shaped and sized to engage a tool having mating surfaces to engage and rotate the set screws 38 such that they will engage the first and second legs 32A and 32B of the cross link body 28. In practice, the link arms 26A and 26B can be adjusted relative to the first and second legs 32A and 32B of the cross link body 28 and then fixed into position when set screws 38 are rotated into a position to engage and lock the components together.

Link arms 26A and 26B each have a C shaped opening 40 at their distal ends which are sized and configured to receive the spinal rod 6. Each link arm 26A and 26B includes a passageway that extends from its upper to lower surface. Contained within each passageway is a clamp screw 42, a compression spring 44 and a rod clamp 46. During assembly, the clamp screw 42 is positioned downward from the upper surface and into the link arm 26A and 26B. A coil compression spring 44 is then positioned from the lower side of the link arm (26A, 26B) and into the passageway. One end of the compression spring 44 bears against a land within the passageway and the opposite end of the compression spring 44 bears against a land located on the rod clamp 46. The rod clamp 46 is located within a recess formed on the lower surface of the link arm (26A and 26B) such that as the clamp screw 42 is rotated the rod clamp 46 will not rotate with it and the clamp screw 42 will thread into the rod clamp 46. The compression spring 44 urges the rod clamp 46 into a spring loaded forward position which is preset prior to implantation. This arrangement achieves a snap on effect between the spinal rod 6 on to the adjustable link arms (26A, 26B) thereby increasing the ease of installation. Once the spinal rod 6 has been snapped on the link arm (26A, 26B) the clamp screw 42 is tightened with a tool having a complimentary engaging surface until the rod 6 is firmly engaged by the C shaped opening 40 and the rod clamp 46.

FIG. 4 is a cross sectional side view of the spinous process cross-link implant with the adjustable link arms in their fully extended position. In this view it is possible to see that the upstanding end portions 36A and 36B on first and second legs 32A and 32B cooperate with set screws 38 and serve as stop members to limit the outward positioning of the link arms 26A and 26B relative to the cross link body 28.

Figure 5:
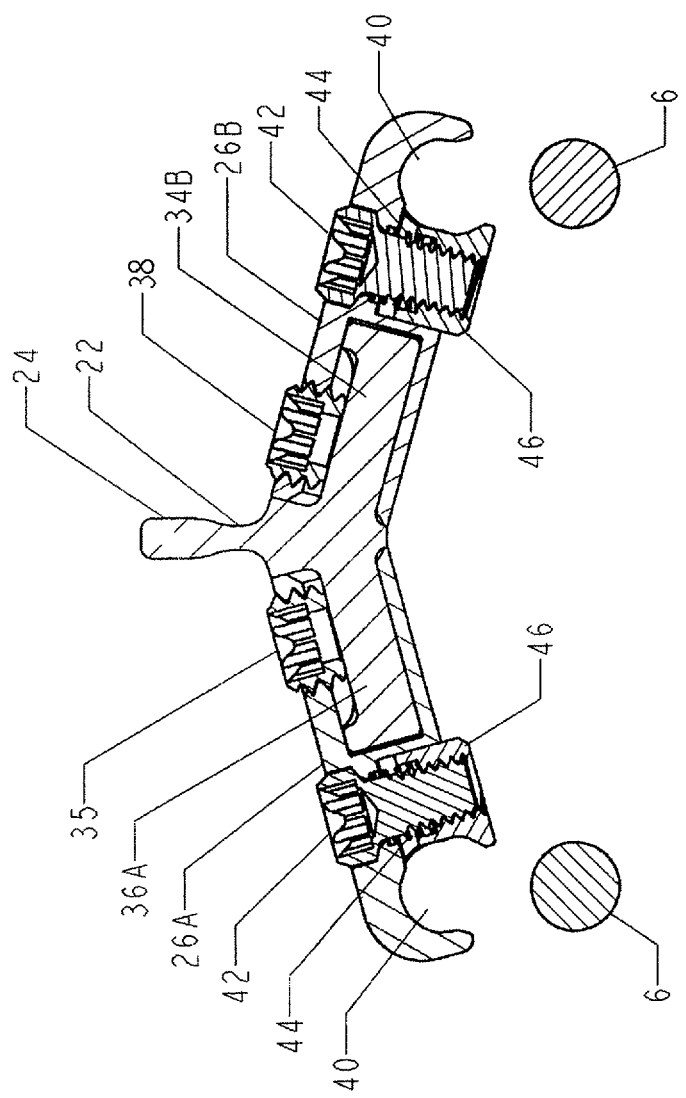
FIG. 5 is a side cross sectional side view of the spinous process cross-link implant in a preassembled position prior to attachment of the adjustable link arms to their respective spinal rods.

FIG. 5 is a side cross sectional side view of the spinous process cross-link implant 20 in a preassembled position prior to attachment of the adjustable link arms 26A and 26B to their respective spinal rods 6. As can be seen in this view the clamp screw 42 is not yet fully threaded into the rod clamp 46.

Figure 6A:
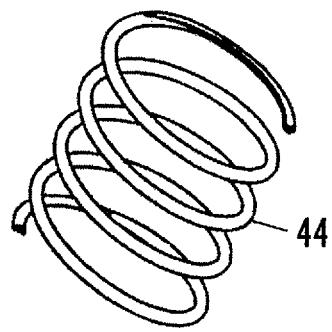
FIG. 6A is an illustration of the compression spring.
Figure 6B:
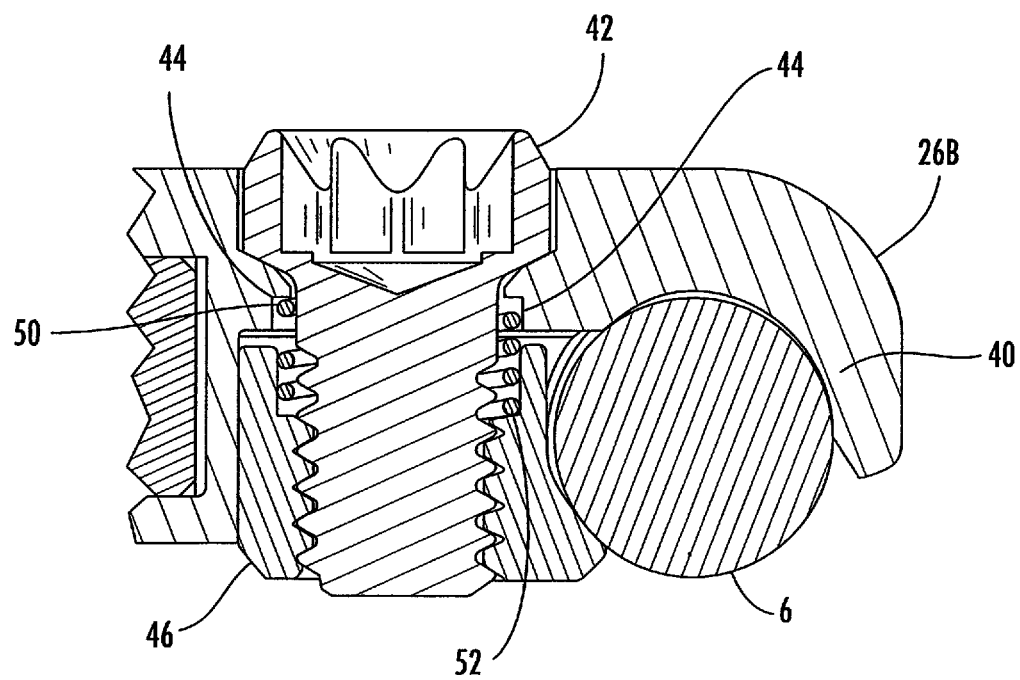
FIG. 6B is a detailed cross sectional side view of an adjustable link arm, spinal rod, camp screw, and rod clamp with compression spring.

FIG. 6B is a detailed cross sectional side view of an adjustable link arm (26A, 26B), spinal rod 6, clamp screw 42, and rod clamp with compression spring 44. As illustrated, link arm (26A, 26B) includes a C shaped opening 40 that is sized and configured to operatively engage spinal rod 6. The link arm (26A, 26B) also includes a passageway that is configured to receive clamp screw 42 through the upper surface and to receive a rod clamp 46 and helical compression spring 44 through the lower surface of the link arm. The compression spring 44 bears at one end thereof against a land 50 within the passageway and against a land 52 formed on the rod clamp member 46 at the opposite end. The clamp screw 42 includes male threads 56 that are threaded into female threads 54 formed on rod clamp 46. Prior to implantation, the clamp screw 42 is partially threaded on to the rod clamp 46. The rod clamp 46 is therefore preset in a spring loaded forward position to minimize the handling, positioning and capturing of the spinal rod 6 between the C shaped opening 40 and the rod clamp 46. The nature of this relationship provides a snap on effect between the link arm (26A, 26B) and the spinal rod 6. Once the rod 6 is snapped into position within the C shaped opening 40 the clamp screw 42 is tightened down to secure the rod into a fixed position.

Figure 8:
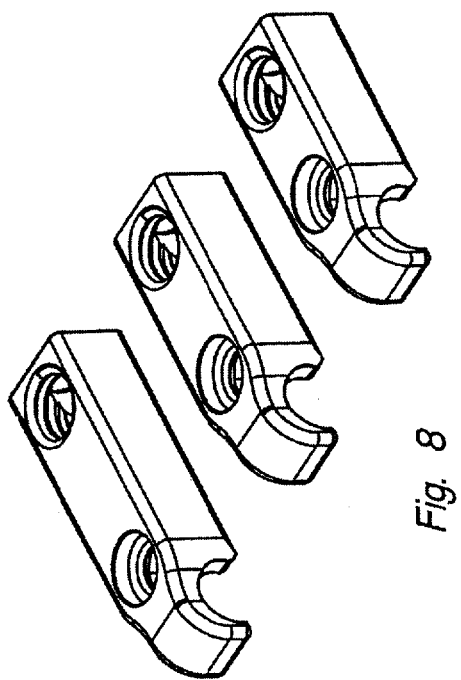
FIG. 8 is an illustration of various size adjustable link arms.
Figure 7:
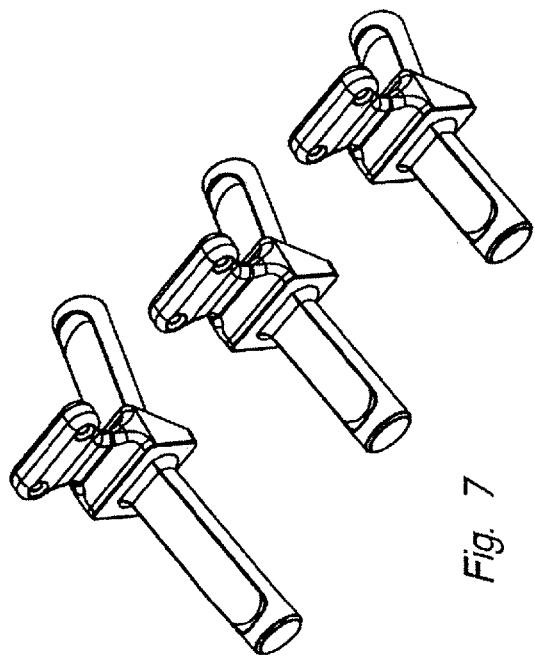
FIG. 7 is an illustration of various size yoke that include a spinous process portion.

FIG. 7 is an illustration of various sized cross-link bodies 28 that include a spinous process yoke 22. The appropriate sized cross-link body 28 will be selected based on the anatomical configuration at the point of application. In a similar fashion, FIG. 8 illustrates various sized link arms 26A, and 26B.

Figure 9:
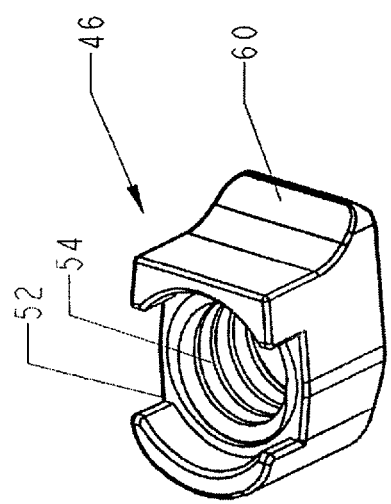
FIG. 9 is a top perspective view of the rod clamp including a foot clamp to operatively engage the spinal rod.

FIG. 9 is a top perspective view of the rod clamp 46. Rod clamp 46 includes an inclined surface that serves as a foot clamp 60 to engage and then, as the clamp screw 42 is threaded into the rod clamp 46, secure the spinal rod 6 to the link arm (26A, 26B). Also shown in this view is land 52 on the rod clamp 46 as well as the female threads 54.

FIG. 10 is a top view of the spinous process implant and illustrating the adjustable orientation of the spinal rods 6 to the adjustable link arms (26A, 26B) due to the conical surfaces within the C shaped clamps. FIG. 11 is a side view of the spinous process implant and illustrating the adjustable orientation of the spinal rods to the adjustable link arms due to the conical surfaces within the C shaped clamps and FIG. 12 is a perspective view of the spinous process implant and illustrating the adjustable orientation of the spinal. As illustrated in the aforementioned figures, the C shaped opening 40 is comprised of two conical surfaces 64A and 64B that come together at the mid point of the C shaped opening 40. The conical surfaces diverge from the mid point of the C shaped opening 40 at approximately a ten degree angle with respect to a longitudinal center line of the C shaped opening. This ten degree conical zone on both sides of the mid point allows the link arm (26A, 26B) to be adjusted relative to the spinal rod 6 thereby reducing the load and stress placed upon the system components.

FIG. 13 is bottom view of the adjustable link arm (26A, 26B) showing the conical surfaces within the C-shaped opening 40 and the rod clamp 46. The rod clamp 46 is positioned within a recess 62 formed in the lower surface of the link arm (26A, 26B). The recess 62 is sized and configured to allow the rod clamp 46 to pivot five degrees in either direction from a centerline that is perpendicular to the longitudinal center line of the C shaped opening 40. Allowing the rod clamp 46 to pivot within the recess 62 enables the link arms (26A, 26B) to be adjusted relative to the spinal rod 6 thereby reducing the load and stress placed upon the system components.

Figure 14:
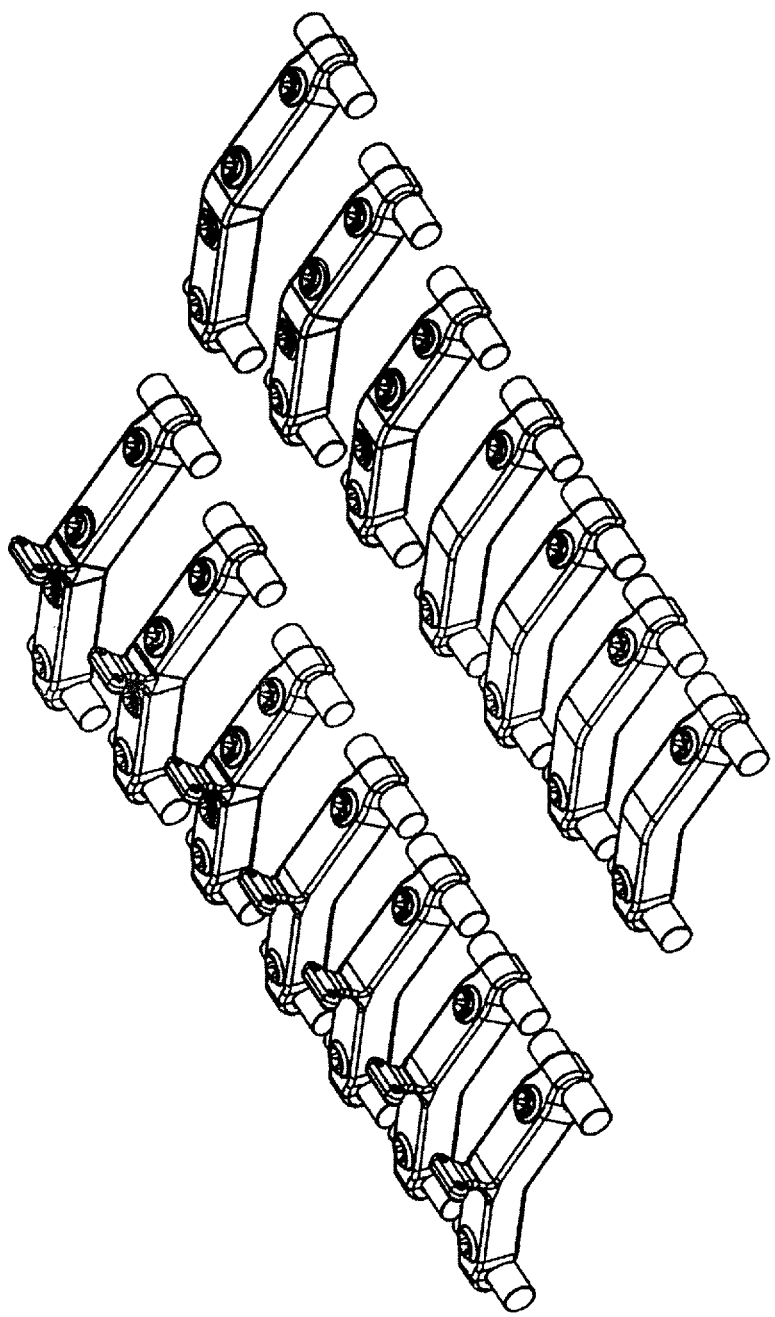
FIG. 14 is a perspective illustration of a kit including a set of spinous process type yokes and bridge type yokes each set including both fixed and variable sized implants.

FIG. 14 is a perspective illustration of a kit including a set of spinous process type yokes and bridge type yokes each set including both fixed and variable size implants. The set includes fixed yokes that are 25 mm, 26 mm, 27 mm, and 28 mm. One group of this size includes a spinal process yoke and one group has a bridge type yoke. The set also includes variable yokes of 28-31 mm, 31-36 mm, and 36-45 mm. Similarly, one group of these sizes includes a spinal process type yoke and one group includes a bridge type yoke. Typically, these yoke would be used with a 3.5 mm spinal rod but rods of other diameters could be used as well.

Figure 15:
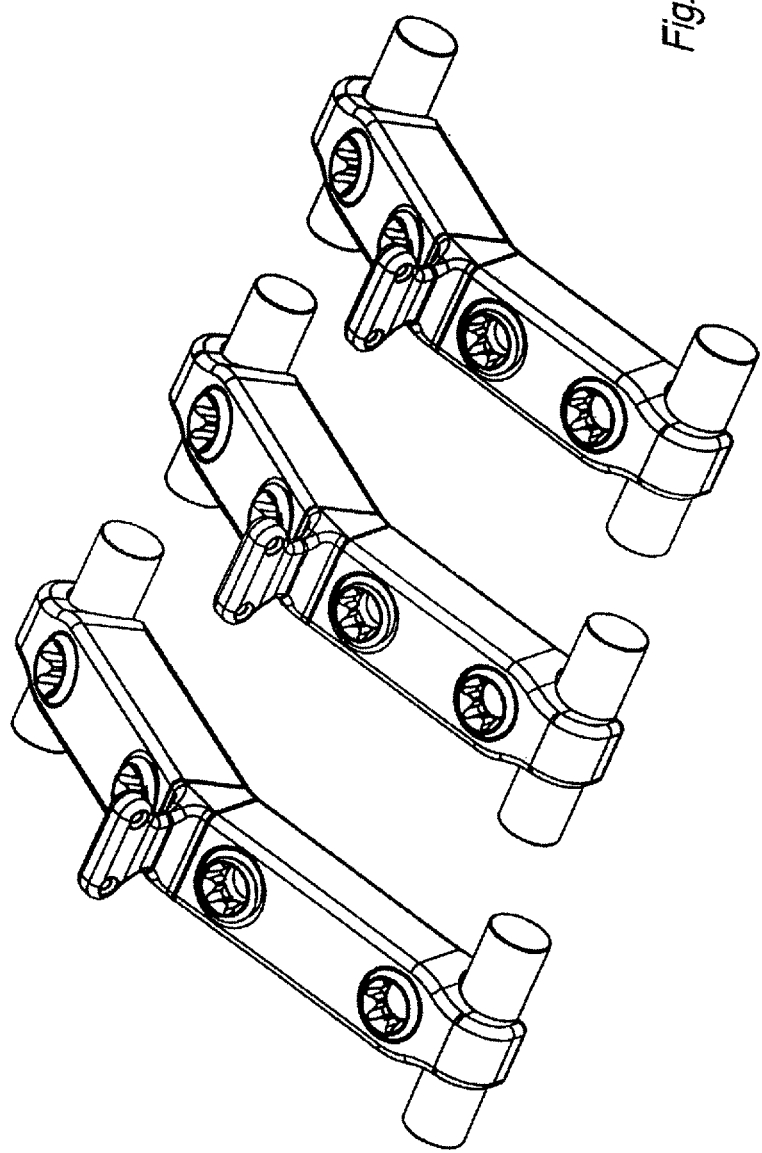
FIG. 15 illustrates a set of spinous type yoke of varying sizes that are configured to cooperate with a 5.5 mm spinal rod.

FIG. 15 illustrates a set of spinous type yoke of varying sizes that are configured to cooperate with a 5.5 mm spinal rod. By way of example, the smaller yoke can vary in the range of 44-52 mm, the next larger in the range of 52-66 mm and the largest of the group adjustable within the range of 66-91 mm.

FIG. 16 is an exploded perspective view of a spinal process insert and a yoke body with an insert pocket. In this embodiment the spinous process cross-link implant 120 includes a cross link body 128. Cross-link body 128 includes a central portion 130 that is generally wedge shaped in cross section. The upper portion of the central body 130 includes an insert pocket 132. The pocket 132 extends between the front and rear faces of the central body 130 and includes a bottom surface 134 and contiguous side walls 136A and 136B that converge as they rise from the bottom surface 134 towards the open end of the pocket 132. In this embodiment the prosthetic spinous process is not molded as part of the cross link body 128 but rather is formed as an insert 140 that is positioned with the pocket 132. This modular yoke arrangement permits the yoke to be used with various sized and shaped spinal process inserts. The spinous process insert 140 may be formed from any suitable material such as peek or biocompatible plastic. The spinous process 140 is positioned within the pocket 132 and is affixed in place. The prosthetic spinous process 140 includes a plurality of apertures 124 that allow sutures to pass through for closure and reattachment of the lumbar fascia and paraspinal muscles following the lumbar laminectomy procedure. The insert 140 can be press fit or welded into the pocket 132 in a factory environment or crimped into place in the field.

FIG. 18 is a perspective view of several yoke bodies each having a spinal process inserts of varying profile and vertical height. FIG. 19 is a side view of the yoke bodies of FIG. 18. As shown in these figures spinal process inserts 140A, 140B and 140C each have a different profile and a different vertical height. The interchangeability of the spinous process inserts allows the surgeon to select the best fit for the patient based upon the anatomical configurations presented by the patient.

FIGS. 20 and 21 depicts a yoke 200 having fixed link arms 202 and 204. In this embodiment the spinous process insert 206 is either permanently attached to the link arms or formed integral thereto.

FIG. 21-28 depicts another embodiment having a spinous process insert 220 with a adjustable link arms 222 and 224 having upper set screws 226 for securement to the yoke body 228. In this embodiment, set screws 230 are employed for attaching to a rod wherein the set screw 230 engages a rod 235 and forcing the rod into a hook shaped 232 link arm cavity to prevent movement.

Figure 31:
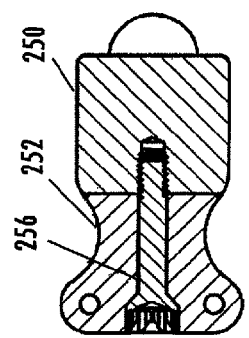
FIG. 31 is a end view of FIG. 30.
Figure 29:
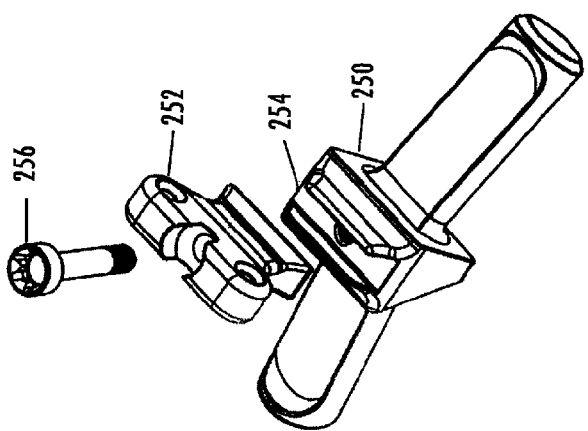
FIG. 29 is an exploded view of the yoke attached to the link arm by use of a fastener.
Figure 30:
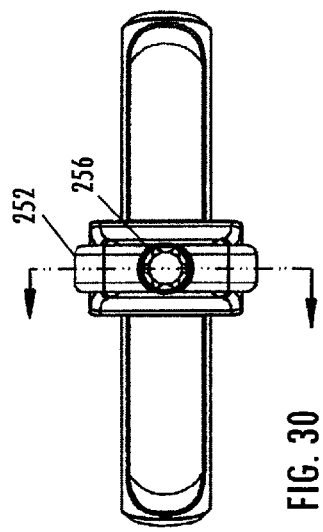
FIG. 30 is a top view of FIG. 29.

FIG. 29-31 illustrates a yoke 250 having a spinous insert 252 securable within receptacle 254 by locking fastener 256. The spinous insert attachment illustrates an example of attachment allowing the surgeon to chose different spinous inserts and secure the inserts before use. For instance, the spinous insert may employ three or more apertures, as opposed to the two apertures depicted, that allow sutures to pass through for closure and reattachment of the lumbar fascia and paraspinal muscles following the lumbar laminectomy procedure. The fastern attachment depicting another embodiment in addition to the previously described press fit, weldment or crimped into place in the field type attachment.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

What is claimed is:

1. A prosthetic spinous process cross-link implant for the replacement of a posterior vertebral element, wherein the vertebral element includes a natural lamina extending from a pair of natural pedicles and a natural spinous process extending from the lamina, the prosthetic spinous process cross-link implant for use with a pair of spinal rods configured for being attached to at least two adjacent vertebral bodies by pedicle screws;

said spinous process cross-link implant including a cross link body having a first leg extending outwardly from a central portion to a first distal end and a second leg extending outward from said central portion to a second distal end, wherein said central portion comprises a generally wedge shaped cross section which tapers from a larger width at a posterior end of the central portion to a smaller width at an anterior end of the central portion and includes a prosthetic spinous process located posteriorly above said central portion and each said distal end having an upstanding end portion;

said spinous process cross-link implant further including a pair of link arms each having a bore, one of said pair of link arms being slidably attached to said first leg and the other of said pair of link arms being slidably attached to said second leg, said upstanding end portions preventing said first and second leg from being completely withdrawn from said pair of link arms, each of said link arms having a C shaped opening sized and configured to receive and secure one of said pair of spinal rods, each of said link arms are independently adjustable to different anatomical configurations with respect to said first and second leg;

said spinous process cross-link implant further including a clamp screw and a rod clamp that are threadably engaged to one another within a passageway in each one of said pair of link arms;

whereby when one of said pair of spinal rods is positioned in said C shaped opening of one of said pair of link arms and said clamp screw is threaded down into said rod clamp said one of said pair of spinal rods will be tightly secured to said one of said pair of link arms.

2. The prosthetic spinous process cross-link implant of claim 1 further including a set screw that is threaded into each one of said pair of link arms, said set screw having a first end that is configured to engage an operating tool that will rotate said set screw and thread it into the each one of said pair of link arms, said set screw having a second end that extends into said bore of each one of said link arms, said second end having a planar surface that frictionally engages a groove on one of said first and second legs of the cross link body member and retain said one of said first and second legs in a fixed position relative to one of said pair of link arms.

3. The prosthetic spinous process cross-link implant of claim 2 wherein acts as a stop element and prevents either the first or second leg from being completely withdrawn from one of said pair of link arms.

4. The prosthetic spinous process cross-link implant of claim 1 wherein the prosthetic spinous process includes one or more apertures extending through the prosthetic spinous process.

5. The prosthetic spinous process cross-link of claim 4 wherein said one or more apertures serve as an attachment site for the re-attachment of tissue.

6. The prosthetic spinous process cross-link implant of claim 5 wherein said implant is comprised of a material allowing for the reattachment and regrowth of bone.

7. The prosthetic spinous process cross-link implant of claim 1 further including a spring positioned within each one of said link arms, said spring having a first end that bears against a land within said passageway and a second end that bears against a land formed on said rod clamp member, wherein prior to implantation, the clamp screw is partially threaded on to the rod clamp and the rod clamp is therefore preset in a spring loaded forward position to minimize the handling, positioning and capturing of the spinal rod between the C shaped opening and the rod clamp and provides a snap on effect between one of said pair of link arms and one of said spinal rods.

8. The prosthetic spinous process cross-link implant of claim 1 wherein the rod clamp includes an inclined surface that serves as a foot clamp to engage and then, as the clamp screw is threaded into the rod clamp, secure one of the pair of spinal rods to one of said pair of link arms.

9. The prosthetic spinous process cross-link implant of claim 1 wherein the rod clamp is positioned within a recess formed in a lower surface of each of said pair of link arms, wherein said recess is sized and configured to allow the rod clamp to pivot approximately five degrees in either direction from a centerline that is perpendicular to a longitudinal center line of the C shaped opening, thereby allowing the rod clamp to pivot within the recess and enable each of said pair of link arms to be adjusted relative to the spinal rod thereby reducing the load and stress placed upon the system components.

10. The prosthetic spinous process cross-link implant of claim 1 wherein said C shaped opening includes two conical surfaces that come together at the midpoint of the C shaped opening, said conical surfaces diverging from the midpoint of the C shaped opening at approximately a ten degree angle with respect to a longitudinal center line of the C shaped opening, whereby a zone defined by the ten degree angle on both sides of the midpoint allows each of said pair the link arms to be adjusted relative to the spinal rod thereby reducing the load and stress placed upon the system components.

11. The prosthetic spinous process cross-link implant of claim 1 wherein a plurality of spinous process cross-link implants can be assembled as a kit and said kit includes a group of spinous process type yokes and bridge type yokes each group including both fixed and variable sized implants.

12. The prosthetic spinous process cross-link implant of claim 1 wherein said prosthetic spinous process is a prosthetic spinous process insert located in a pocket formed in the posterior end of the central portion of the cross link body.

13. The prosthetic spinous process cross-link implant of claim 12 wherein said spinous process insert is selected from a group of spinous process inserts of varying profiles and vertical heights.

14. The prosthetic spinous processes cross-link implant of claim 12 wherein said spinous process insert is formed from PEEK or biocompatible plastic material.

15. The prosthetic spinous process cross-link implant of claim 12 wherein said spinous process insert is press fitted or welded into said pocket in a factory environment or crimped into place in the field.

* * * * *